US011160892B2

(12) United States Patent
Baumgartner et al.

(10) Patent No.: US 11,160,892 B2
(45) Date of Patent: Nov. 2, 2021

(54) ULTRASONIC STANDING WAVE NEBULIZATION SYSTEM

(71) Applicant: RESTEC SOLUTIONS, LLC, Port Saint Lucie, FL (US)

(72) Inventors: Paul Baumgartner, Port Saint Lucie, FL (US); Currie P. Crookston, Pittsburgh, PA (US)

(73) Assignee: RESTEC SOLUTIONS, LLC, Port Saint Lucie, FL (US)

(*) Notice: Subject to any disclaimer, the term of this patent is extended or adjusted under 35 U.S.C. 154(b) by 170 days.

(21) Appl. No.: 16/789,330

(22) Filed: Feb. 12, 2020

(65) Prior Publication Data

US 2020/0254124 A1 Aug. 13, 2020

Related U.S. Application Data

(60) Provisional application No. 62/804,939, filed on Feb. 13, 2019, provisional application No. 62/864,350, filed on Jun. 20, 2019.

(51) Int. Cl.

| | |
|---|---|
| *A61L 2/22* | (2006.01) |
| *B01B 1/00* | (2006.01) |
| *B01D 53/26* | (2006.01) |
| *A61L 2/26* | (2006.01) |

(52) U.S. Cl.

CPC .................. *A61L 2/22* (2013.01); *A61L 2/26* (2013.01); *B01B 1/005* (2013.01); *B01D 53/265* (2013.01); *B01D 53/266* (2013.01); *A61L 2202/11* (2013.01); *A61L 2202/122* (2013.01); *A61L 2202/14* (2013.01)

(58) Field of Classification Search

CPC .......... A61L 2/22; A61L 2/26; A61L 2202/11; A61L 2202/122; A61L 2202/14; B01B 1/005; B01D 53/265; B01D 53/266

See application file for complete search history.

(56) References Cited

U.S. PATENT DOCUMENTS

| | | |
|---|---|---|
| 4,836,684 A | 6/1989 | Javorik et al. |
| 7,641,130 B2 | 1/2010 | Ricciardi et al. |
| 8,382,008 B1 | 2/2013 | Ricciardi et al. |
| 9,376,857 B1 | 6/2016 | Baumgartner et al. |
| 9,551,996 B2 | 1/2017 | Baumgartner et al. |

(Continued)

OTHER PUBLICATIONS

George K. Lewis, Jr. and William L. Olbricht, "Design and Characterization of a High-Power Ultrasound Driver with Ultralow-Output Impedance", Review of Scientific Instruments 80, 114704, Nov. 10, 2009, pp. 114704-1 thru 114704-8.

(Continued)

*Primary Examiner* — Sean E Conley

(74) *Attorney, Agent, or Firm* — David R. Heckadon; Gordon Rees Scully Mansukhani LLP

(57) ABSTRACT

A system of generating an aerosol, by: (a) placing a liquid into a liquid chamber in an ultrasonic nebulization system having a cylindrical aerosol production chamber received within a cylindrical master chamber, and having top and bottom ultrasonic transducers; (b) passing air up through the aerosol production chamber; and (c) producing acoustic standing waves above the surface of the liquid with the top and bottom ultrasonic transducers, thereby generating an aerosol of the liquid by action of the standing waves.

20 Claims, 9 Drawing Sheets

(56) References Cited

U.S. PATENT DOCUMENTS

| | | |
|---|---|---|
| 9,789,508 B2 | 10/2017 | Baumgartner et al. |
| 10,029,274 B1 | 7/2018 | Baumgartner et al. |
| 10,517,977 B2 | 12/2019 | Sakaki |
| 2008/0047575 A1 | 2/2008 | Puskas |
| 2008/0233001 A1* | 9/2008 | Ricciardi ............... A61L 9/122 422/20 |
| 2012/0167914 A1 | 7/2012 | Obweger et al. |
| 2013/0008473 A1 | 1/2013 | Tuziuti et al. |
| 2017/0066003 A1 | 3/2017 | Baumgartner et al. |

OTHER PUBLICATIONS

C. R. P. Courtney, C.-K. Ong, B. W. Drinkwater, P.D. Wilcox, C. Demore, S. Cochran, P. Glynne-Jones and M. Hill, "Manipulation of Microparticles Using Phase-Controllable Ultrasonic Standing Waves", The Journal of the Acoustical Society of America 128 (4), EL195, Sep. 10, 2010, pp. EL195 thru EL199.

International Searching Authority, International Search Report and Written Opinion for corresponding International Application No. PCT/US2020/017920, dated Apr. 16, 2020, 7 pages.

\* cited by examiner

ULTRASONIC STANDING WAVE NEBULIZATION SYSTEM

RELATED APPLICATIONS

The present application claims priority to U.S. Provisional Patent Application 62/804,939, entitled Ultrasonic Standing Wave Nebulization System, filed Feb. 13, 2019, and U.S. Provisional Patent Application 62/864,350, also entitled Ultrasonic Standing Wave Nebulization System, filed Jun. 20, 2019, the entire disclosures of which are incorporated herein by reference in their entireties.

TECHNICAL FIELD

The present invention relates to ultrasonic nebulizers for aerosol production and to aerosol disinfection treatment chambers.

BACKGROUND OF THE INVENTION

Traditional ultrasonic nebulizers are used to generate aerosols that can then be used for disinfection in aerosol treatment/sanitation chambers. Unfortunately, these traditional ultrasonic nebulizers all tended to be somewhat limited in their aerosol production output. It would instead be desirable to provide a system having increased productive capacity. In addition, the existing ultrasonic nebulizers all tend to require a long time to "recover" (i.e. to remove condensation from the equipment to "reset" the system) between disinfection uses. It would instead be desirable to reduce the recovery time between system uses.

SUMMARY OF THE INVENTION

The present system provides a novel ultrasonic system and method to generate aerosols from liquids. One advantage of the present system is that it generates significantly increased production of aerosols as compared to traditional ultrasonic nebulizers that simply rely on air moving across the surface of the liquid. In contrast, the present system achieves enhanced aerosol production by using a pair of ultrasonic transducers positioned at respective top and bottom ends of an aerosol production chamber which then generate acoustic standing waves therebetween. These standing waves are nodes of concentrated areas of high and low air pressures. As air passes up into the region of the standing wave in the aerosol production chamber (i.e.: as the moist air passes up through regions of alternating high and low air pressures), the action of these standing waves substantially increases the production of the aerosols, as will be fully explained.

The present system also provides a novel apparatus to carry out this preferred method. In preferred aspects, the main physical components of the present aerosol production system use a "nesting" design where different cylindrical components are positioned together to build the system. In one preferred embodiment, an aerosol production chamber is positioned within a master chamber. This master chamber has a liquid chamber at its bottom with a bottom ultrasonic transducer positioned below the liquid chamber. A nesting baffle preferably assembly stands within the aerosol production chamber to support the aerosol chamber and to create an air passage under the aerosol production chamber to permit air to pass through before entering the bottom of the aerosol production chamber. This intake air passes across the surface of the liquid in the liquid chamber. In operation, air is pumped down through the master chamber (passing between the walls of the master chamber and aerosol production chamber) and then up into the aerosol production chamber. Positioned at the top of the aerosol production chamber is the top ultrasonic transducer. Preferably, the top ultrasonic transducer is suspended from a monitor assembly. In optional embodiments, this monitor assembly may also include a cover that covers both the tops of the aerosol production chamber and the master chamber and thus also seals the air paths both into and out of the aerosol generating system.

In optional embodiments, a preferred method of operation includes varying the output frequency of the bottom ultrasound transducer while the node phase position of acoustic waveform is monitored by the top transducer to produce and maintain a standing wave pattern in the aerosol production chamber. (In optional embodiments, the frequency of the top ultrasound transducer may be varied as well). Preferably, low humidity air enters at the bottom of the aerosol production chamber and the resulting high humidity aerosol exits at the top center of the device (i.e.: above the top ultrasound transducer and its associated assembly).

In further optional embodiments, a radiation heat source is connected to an adjacent aerosol treatment chamber. This heat source may be used to cause the particles in the treatment chamber to vaporize. This approach has the advantage of decreasing sterilization times. Specifically, such heating of the treatment chamber can advantageously cause the particle size to be reduced from about 3 um by a factor of −10 to about 0.3-0.5 during this transition. As such, the sterilization time can be shortened as much as 50% over non-vaporizing capable treatment chambers. In addition to shortening the sterilization time, this optional irradiation of the aerosol suspended in the treatment chamber also reduces the amount of condensation on the exposed surfaces within the chamber. This results in a shorter "recovery" period between uses of the present system. In various aspects, the optional heating source may be a radiant energy source including RF, IR or visible light range heating. IR light is the most preferable. In preferred configurations, this optional heating source may instead be mounted externally to the aerosol treatment chamber.

In further optional embodiments, a dehumidification and filtration system can also be provided for the air circulating within the aerosol treatment chamber (i.e.: after the produced aerosol has been used in the treatment chamber for sanitation or disinfection). In preferred embodiments, such a dehumidification and filtration system can consist of a combination of Peltier, compressed refrigerant or ventilated dehumidification systems. After the aerosol generation has been completed in the present system, it is desirable to have the system quickly ready itself for another use. In preferred aspects, the present aerosol treatment chamber can be quickly dried out and restored to its original (pre-use) state by dehumidifying and particle filtering the air with the dehumidification and filtering system.

BRIEF DESCRIPTION OF THE DRAWINGS

FIG. 2A is a view corresponding to FIG. 1, showing fresh air flowing into the system (with air flowing down in the spaces between the walls of the master chamber and the aerosol production chamber).

FIG. 2B is a view corresponding to FIG. 2A, but taken at a later period of time when an ultrasonic standing wave is generated in the aerosol production chamber.

FIG. 2C is a view corresponding to FIG. 2B, but taken at a still later period of time when the aerosol generated by the ultrasonic standing wave is removed from the system. (After the aerosol has been removed, it can be directed into the aerosol treatment chamber of FIG. 5, for example, to sterilize objects placed therein).

DETAILED DESCRIPTION OF THE DRAWINGS

Figure 1:
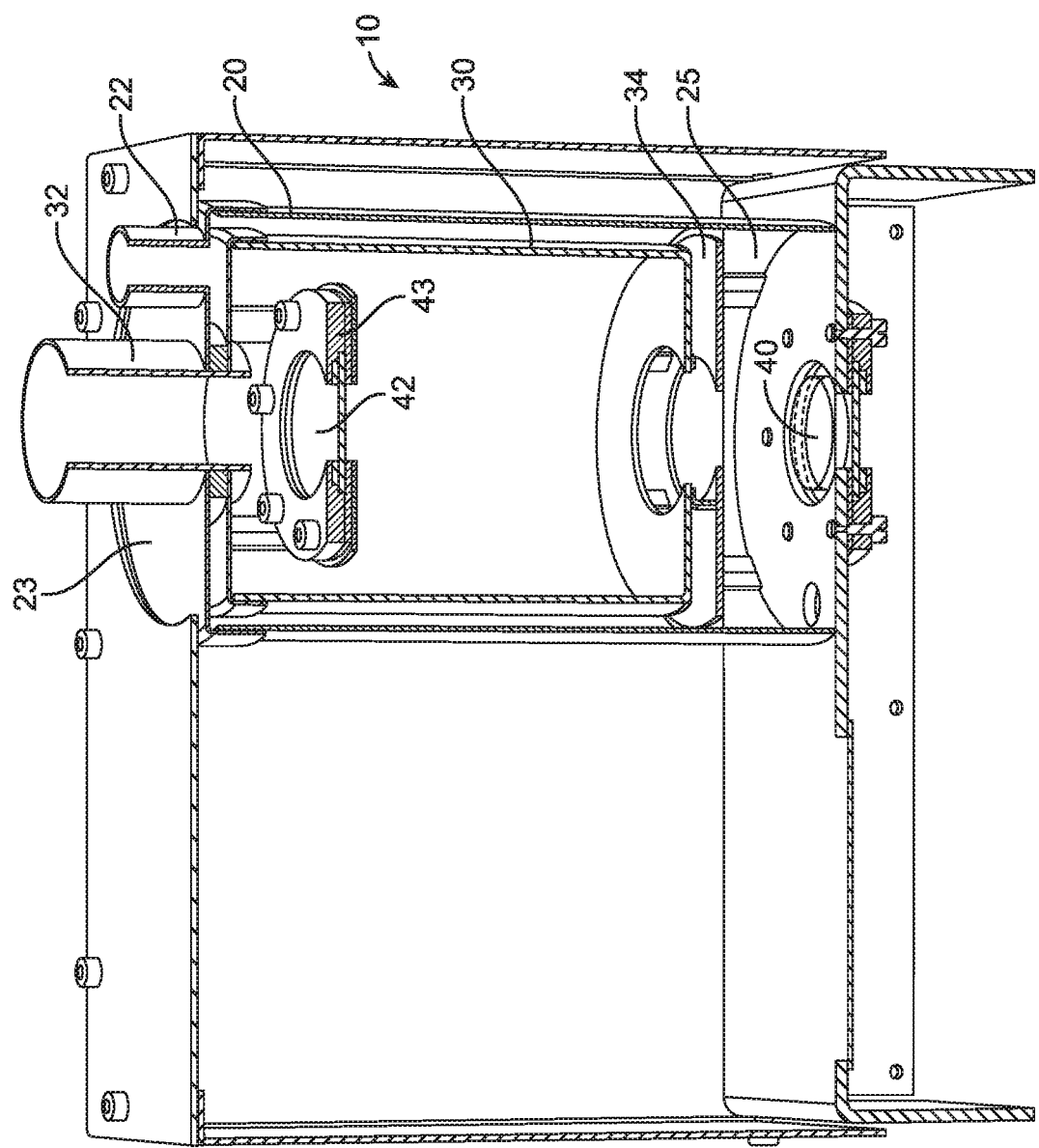
FIG. 1 is a sectional perspective view of a preferred embodiment of the present ultrasonic nebulizing system.
Figure 3A:
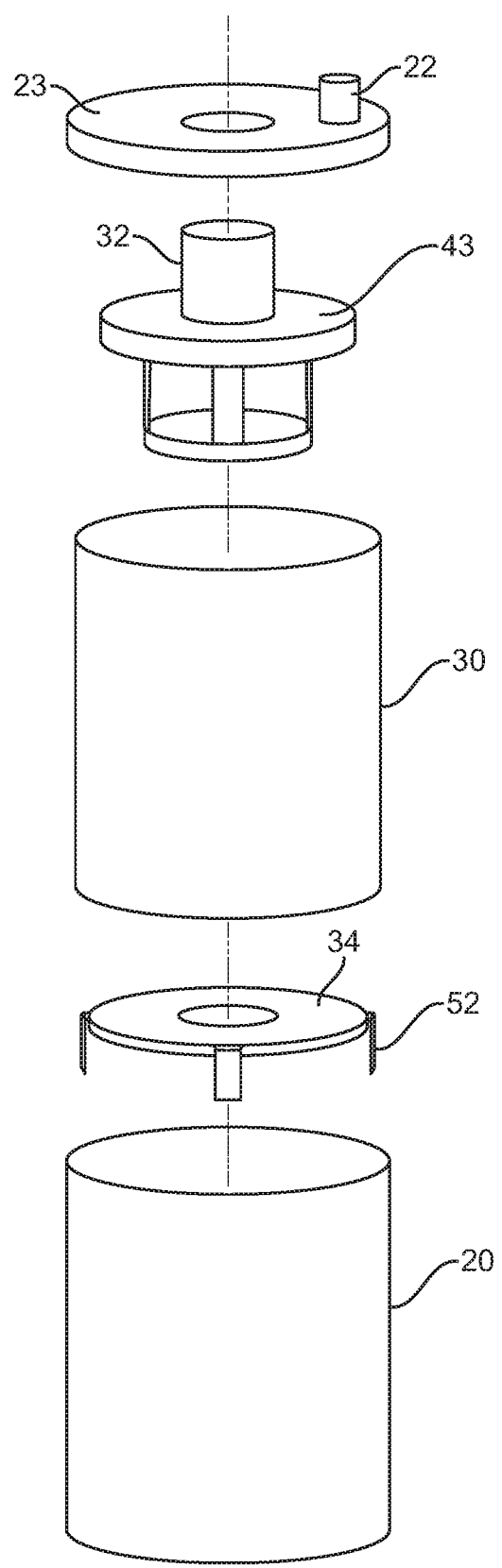
FIG. 3A is an exploded perspective view showing the primary nested components of the present system.
Figure 3B:
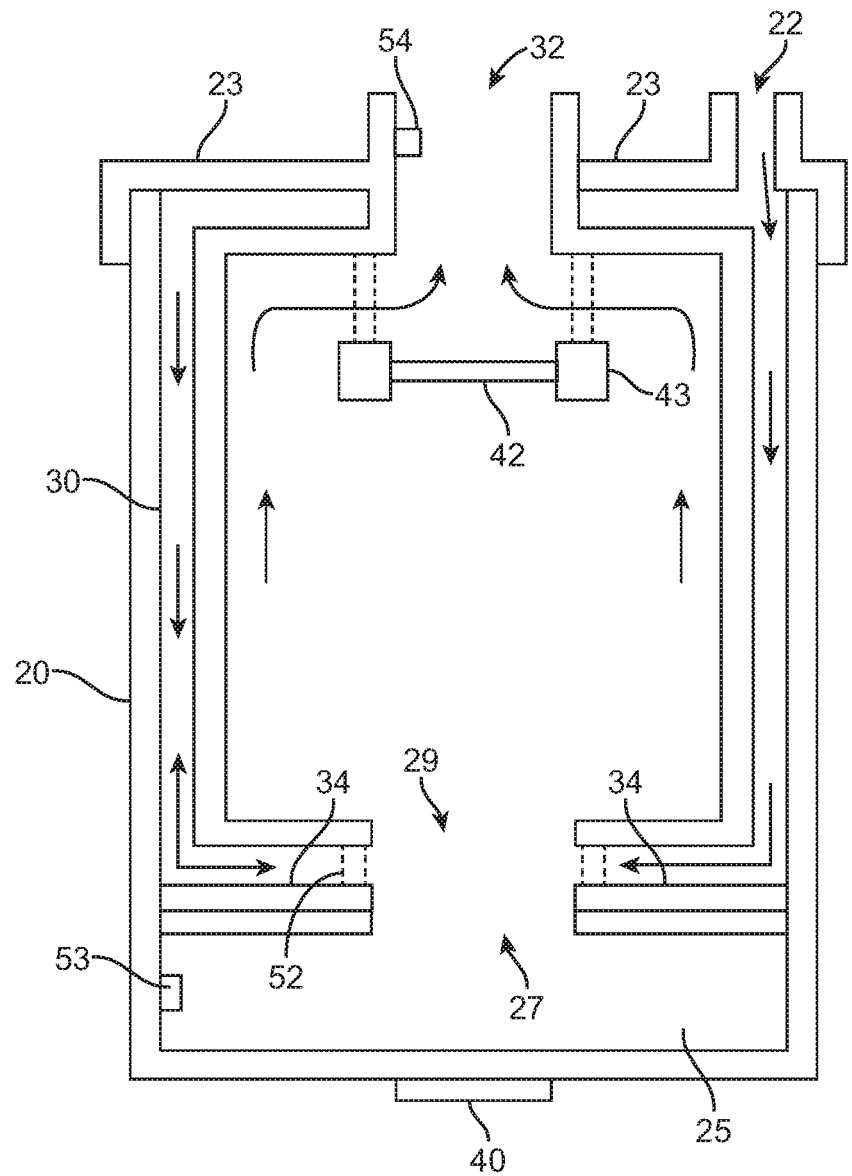
FIG. 3B is a sectional side elevation view of the primary nested components of FIG. 3A.

As seen in FIGS. 1, 3A and 3B, an ultrasonic nebulization system 10 is provided. Ultrasonic nebulization system 10 produces aerosol and preferably comprises: a master chamber 20; an aerosol production chamber 30 received within master chamber 20; an air inlet 22 into master chamber 20; an aerosol outlet 32 out of aerosol production chamber 30; a liquid chamber 25 in the bottom of master chamber 20; a baffle assembly 34 positioned at the bottom of aerosol production chamber 30 above liquid chamber 25 in master chamber 20; a bottom ultrasonic transducer 40 positioned below liquid chamber 25; and a top ultrasound transducer 42 positioned above liquid chamber 25 near the top of aerosol production chamber 30. Top ultrasound transducer 42 is preferably supported by a monitor assembly 43, as will be further explained.

In accordance with the present system, the top and bottom ultrasound transducers 40 and 42 generate standing waves therebetween within aerosol production chamber 30. The present preferred method steps of aerosol generation are illustrated in sequential steps of FIGS. 2A, 2B and 2C, as follows.

Figure 2A:
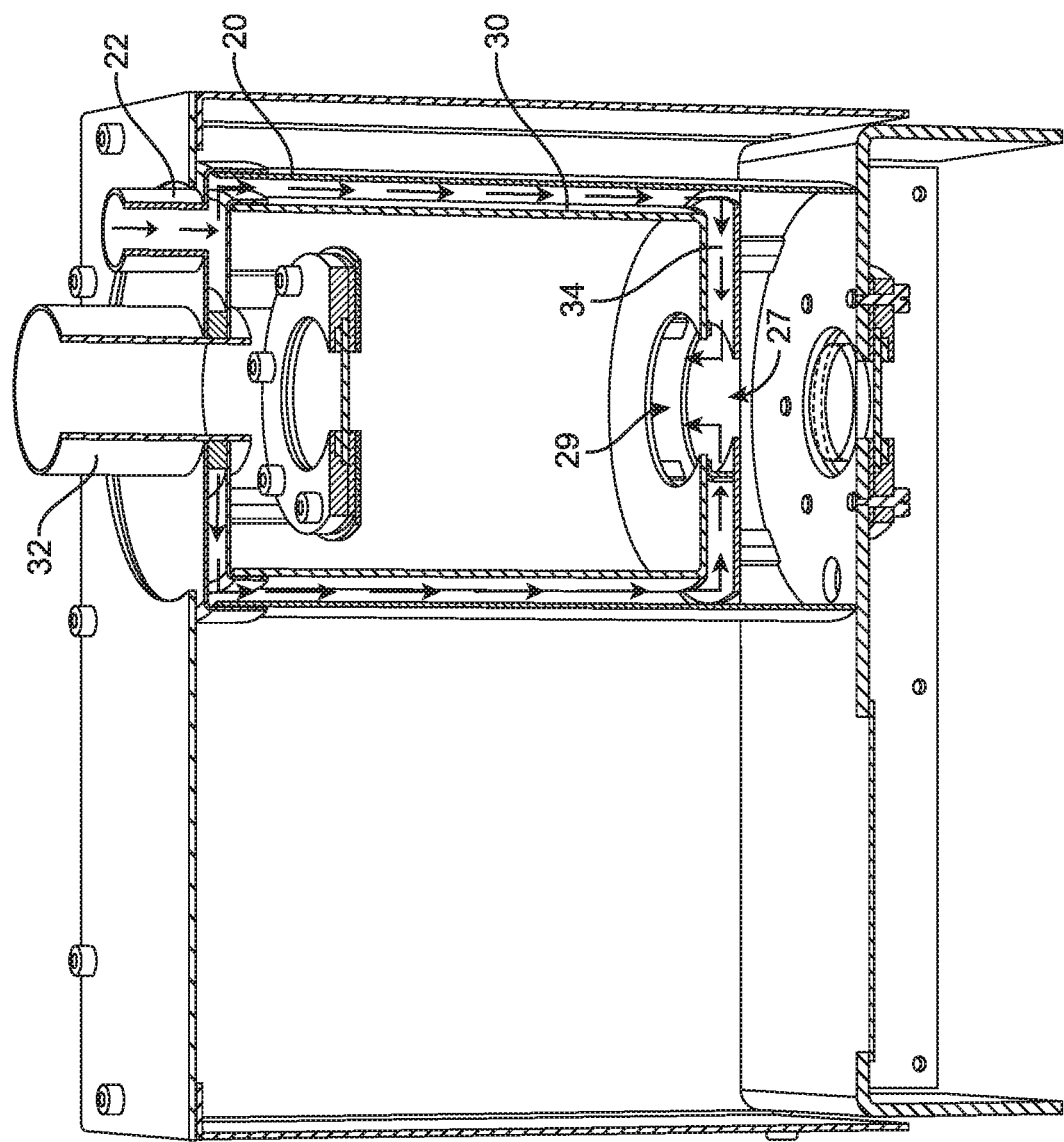
FIGS. 2A to 2C show successive steps in the production of an aerosol, as follows.

FIG. 2A shows fresh air flowing into the system (with air entering air inlet 22 and flowing down between the inner walls of master chamber 20 and outer walls of aerosol production chamber 30). As can be seen, the air then passes over baffle assembly 34 and across the top of liquid chamber 25 (i.e.: above bottom aperture 27 in aerosol production chamber 30). Spacers 52 support on baffle assembly 34 lift aerosol production chamber 30 to provide an air passage thereunder.

Figure 2B:
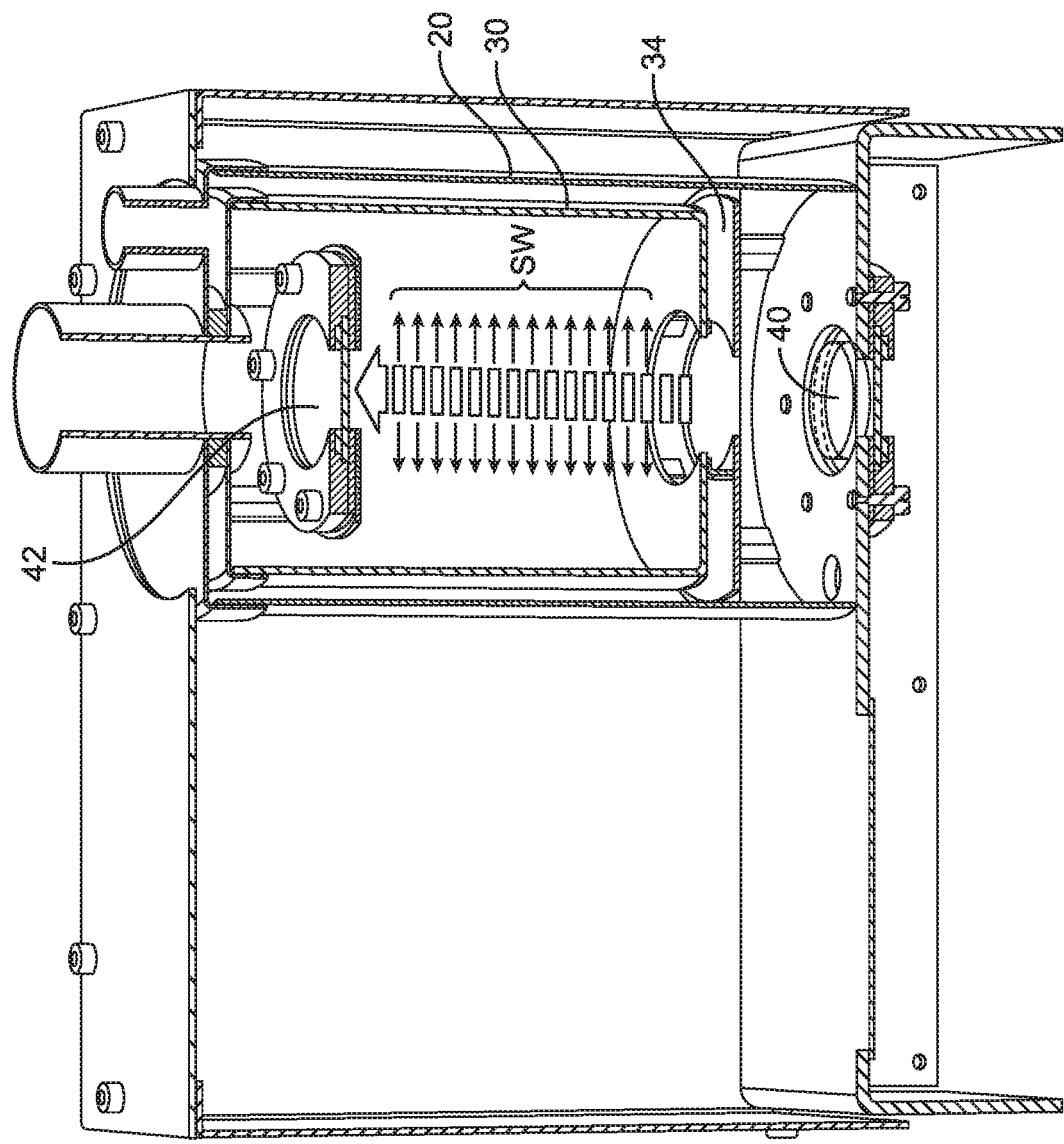

Next, in FIG. 2B, an ultrasonic standing wave SW is then generated by the action of ultrasonic transducers 40 and 42. This ultrasonic standing wave SW generates aerosol as will be further explained.

Figure 2C:
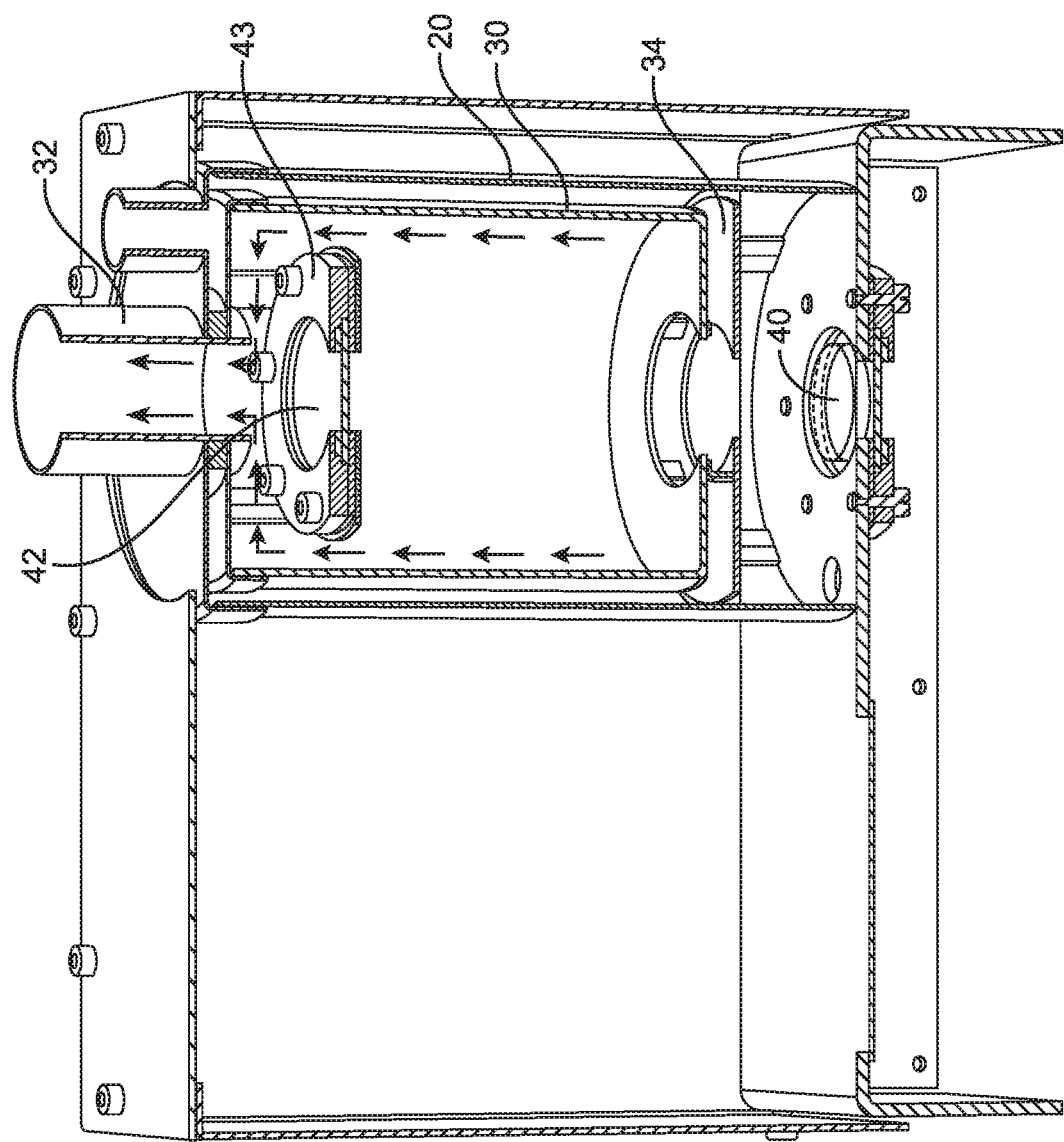

Finally, in FIG. 2C, the aerosol generated by the ultrasonic standing wave is removed from the system, exiting up through the aerosol output 32 which is preferably positioned above monitor assembly 43. In preferred embodiments, monitor assembly 43 supports the top ultrasonic transducer 42.

It is to be understood that the steps illustrated in FIGS. 2A to 2C may be carried out sequentially or simultaneously, all keeping within the scope of the present invention. For example, aerosol may be continuously produced in aerosol production chamber 30 while being continuously drawn out of aerosol outlet 32.

The present system also includes a novel method of generating an aerosol, comprising: placing a liquid into a liquid chamber 25 in an ultrasonic nebulization system 10; passing air up through the aerosol production chamber 30 while generating standing waves above the surface of the liquid in liquid chamber 25. The standing waves are generated by applying an ultrasonic field with an upper ultrasonic transducer 42 and a lower ultrasonic transducer 40; thereby generating the aerosol from the liquid. As illustrated, the standing waves SW are generated in the aerosol production chamber 30 while air is passed through aerosol production chamber 30 and aerosol is expresses in a generally horizontal fashion from the standing wave SW. The aerosol moves to the sides of the chamber and then is moved upwardly out of aerosol production chamber 30 through aerosol output 32.

In further aspects of this preferred method, the frequency of the lower ultrasonic transducer 40 can be adjusted to generate the standing waves that are monitored by the monitor assembly 43 housing top transducer 42 (as will be more fully explained herein).

In further aspects of the preferred method, the temperature in aerosol production chamber 30 is monitored to ensure that critical performance aspects of aerosol generating are functioning.

In further aspects of this preferred method, the liquid level in liquid chamber 25 is maintained at a level that extends up to the bottom aperture 27 of aerosol production chamber 30 (i.e.: just below the space where air passes under baffle assembly 34). This approach minimizes the thermal effects of airflow passing over liquid chamber 25's surface, providing greater liquid temperature regulation. This preferred approach also minimizes acoustic wave energy and harmonics that create liquid perturbation and reservoir cavitation turbulence. Liquid surface disturbances interfere with horizontal airflow entering into the aerosol production chamber.

The preferred "nested" design of the primary components of the present system is best seen in FIGS. 3A and 3B. Specifically, the present "nested" design is achieved wherein the master chamber 20 is cylindrical and the aerosol production chamber 30 is also cylindrical such that the aerosol production chamber 30 is centered within master chamber 20. Preferably, the cylindrical dimensions of the liquid and aerosol production chambers 20 and 30 are both sized and positioned to promote beneficial horizontal wave reflective and harmonic conditions that occur when output oscillating power is applied. The baffle assembly 34 has top spacers 52. The bottom of aerosol production chamber 30 is placed onto spacers 52. Spacers 52 lift aerosol production chamber 30 to provide an air passage underneath it so that air can pass horizontally across it (FIG. 2A). Since the top surface of the liquid in liquid chamber 25 is preferably kept at the same height as the bottom aperture 27 in aerosol production chamber 30, this minimizes air contact across the top of the liquid surface for air coming into master chamber 20. The air entering the air inlet 22 into master chamber 20 passes down the sides of master chamber 20 (i.e.: between the walls of chambers 20 and 30), and then across the surface of baffle assembly 34, then passing up into the bottom of production chamber 30 at lower production chamber opening 29.

During operation, aerosol is generated by the standing waves SW in aerosol production chamber 30 as moist air passes upwardly through aerosol production chamber 30 and out of the aerosol outlet 32. As such, air entering the air inlet 22 (optionally in top cover 23) pushes the aerosol out of the aerosol outlet 32 (also optionally in top cover 23). Aerosol may also optionally be extracted utilizing negative pressure applied at the aerosol output 32.

In preferred embodiments, a bottom temperature sensor 53 may be positioned adjacent to liquid chamber 25 for sensing the temperature of the liquid, and a top temperature sensor 54 may be positioned within the aerosol output 32 above the monitor assembly 43 for sensing the temperature of the exiting aerosol. This temperature monitoring approach is particularly advantageous because aerosol output temperature is a critical system performance measurement. Input air temperature, liquid temperature, and acoustic power levels all affect aerosol output temperature. Therefore, an output temperature that is out of tolerance indicates system operational level performance issues.

In preferred embodiments, the bottom ultrasonic transducer 40 is a piezoelectric disk that is positioned below the liquid in liquid chamber 25. The bottom ultrasonic transducer 40 is energized with sufficient oscillating drive power to generate an aerosol by producing an acoustic energy column that is focused by the upper transducer 42 to produce a "focused standing wave" (FSW). The FSW is a vertical column of acoustic energy, originating at the face of the bottom transducer 40, extending upwards into the center of aerosol production chamber 30. This acoustic energy vertical column jettisons liquid and droplets upwards. The aerosol production chamber 30 preferably has a calibrated height whereby the top of the FSW column collides with a reflection device (i.e.: the top ultrasonic transducer 42). This reflective device (upper transducer 42) is located at a calibrated height for precision node intersect positioning and the monitoring of the standing wave phase relationship. In operation, the incident (forward) acoustical waves are reflected back into the column producing a coincident (i.e.: reverse) acoustic wave. The combination of the incident and coincident acoustic waves form the FSW maximizing horizontal node and anti-node regions at ½ wavelength intervals. These nodal regions achieve maximum particle levitation and expression. The column height of the acoustic standing wave column is directly proportional to the amount of acoustic energy generated by the transducer drive devices.

As a result, the FSW acts as an efficient self-regulating liquid conveyor belt system, moving liquid progressively upward from the liquid chamber 25 at the bottom of aerosol production chamber 30 into the increasingly productive acoustic standing wave thereabove. Liquid particles are forced upwards, and levitated in the low pressure node areas. Cavitation process begins at the bottom of liquid chamber 25 at the ultrasonic transducer 50's face. The cavitation process continues as particles are forced upwards and enter into the subsequent node and antinode areas of the FSW. Aerosol particles are expressed horizontally outwards from liquid column, within the high-energy antinode areas generated in production chamber 30, then mixing with the air entering into the bottom of production chamber 30 and exiting out the top output 32. This FSW column continues to move and produce aerosol particles until the oscillating power is switched off and remaining liquid particles collapse back into fluid chamber 25.

The dimensions, features, and component specifications of the production chamber 30 are selected according to intended applications and desired aerosol production output. Aerosol is expressed from the present assembly 10 when the bottom ultrasonic transducer 40 is energized and airflow is directed through production chamber 30. Performance of the nebulization assembly is measured in liquid consumption over time. Aerosol volume, density, mass, and particle size are controlled and calibrated assembly features.

In preferred embodiments, the present system may include electronic controls, ultrasonic power drivers, transducers, and liquid and airflow components. A power source may also be connected to a line filter input that feeds power supplies and control electronics. Sterilant diluent and drain liquid lines are also preferably included in the present system and may be connected using quick connect fittings. A control cable may also be connected from the system to an analog/TTL interface connector along with software based control connections. The present aerosol production system preferably also contains network and wireless control and monitoring capabilities. Airflow in and out connections are also preferably connected to air inlet 22 and aerosol outlet 32 in the top cover 23 of the aerosol production chamber 30. Liquid supply and drain quick connect fittings can be located in the base's liquid control area.

Fluid level regulation can optionally be achieved utilizing an external sight tube arrangement and ultrasonic level sensor attached to the sight tube. Liquid supply and proportioning can optionally be achieved with peristaltic pumps. Preferably, a pair of peristaltic pumps can be used. The peristaltic pump heads can be installed so that all fluid handling is isolated below the electronic section of the present system. Optionally, some pump modules may feature a single motor dual pump arrangement. When the external sight tube sensor system indicates a low fluid level, the controller can then activate the liquid pumps. Sterilant and diluent liquids can also be metered and proportioned by rotations per minute of the peristaltic pumps. Preferably, sterilant and diluent mixing is accomplished in the tubing arrangement prior to entering the production chamber fluid reservoir.

Optionally, a vulcanized heating pad containing resistive heating elements can sit at the bottom of the liquid chamber 25 to provide temperature regulation. Such a rubberized heating element can be made of chemical resistant material and can optionally contain temperature sensors for precise fluid temperature control.

Figure 4A:
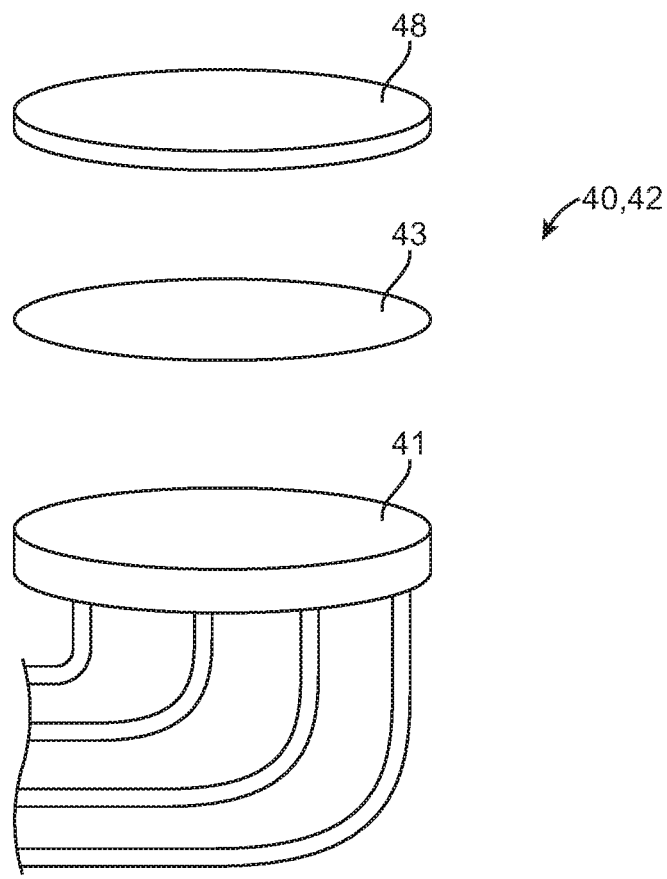
FIG. 4A is an exploded perspective view of an exemplary ultrasonic transducer.
Figure 4B:
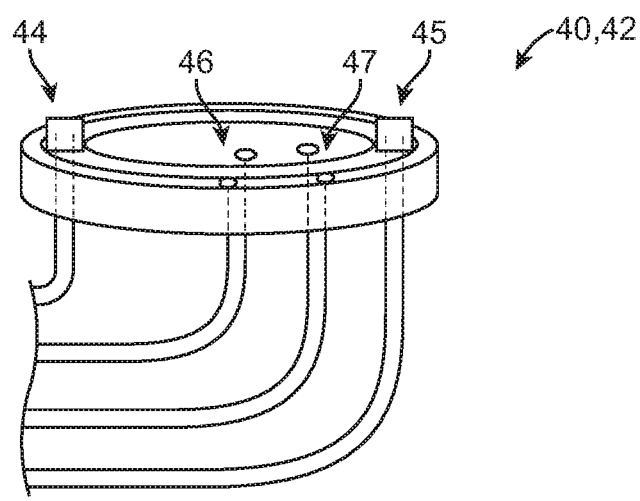
FIG. 4B is an assembled perspective view of an exemplary ultrasonic transducer.

As seen in FIGS. 4A and 4B, the top and bottom ultrasonic transducers 42 and 40 are preferably each flat circular ceramic composite disks. Their operational characteristics are a function of their diameter, thickness and ceramic composition. As seen in FIG. 4A, a final assembled ultrasonic transducer 40, 42 preferably contains a transducer disk 41, and bonded protective coating 43 and a protective layer 48. As seen in FIG. 4B, feedback sensor devices including an amplitude and frequency sensor 44, a thermal sensor 45, and electrical connections including drive power leads 46 and feedback signal lead 47.

Preferably, these sensor components 44, 45 and 47 may be attached to the bottom of ultrasonic transducer 40. These temperature, frequency, and output sensing components 44, 45 and 47 can be attached to the transducer 40 and/or 42 to monitor and ensure performance and component integrity. Power lead attachments 46 can be custom designed and used to connect the drive power wiring to silvered conductive areas of the ultrasonic transducers. This approach improves the integrity of RF power connections and maximizes anode sizing features. Greater anode surface area also improves usable polarized regions of transducer component. This improvement over conventional soldered wire attachment methods is further preferred due to higher than usual component electrical power requirements.

In preferred embodiments, the bonded protective layer (e.g.: glass disk 48) is attached to the top face of the transducer disk 41 that insulates the piezoelectric disk from the liquid reservoir. This protective layer 44 optionally consists of a specific micro thin glass component (<0.014" inch) bonded utilizing a material specific single part UV cured bonding process. This bonded micro thin glass component need not be acoustic wavelength tuned or dependent to the operational frequency generated to produce the FSW.

To electrically drive ultrasonic transducers 40 and 42 and generate optimum FSW conditions, an efficient high-slew rate, pure square wave can be used. A low-impedance, push-pull, high-power FET invertor drive arrangement can optionally also be used. Advantageously, the output power of such invertor drive components can preferably be selected and calibrated for each intended application. This low-impedance ultrasonic power drive arrangement would eliminate conventional impedance matching requirements of a typical amplified drive and load configuration. This greatly improves the efficiency of the power drive delivery and takes advantage of the ultrasonic transducers' high-Q characteristics. In addition, this arrangement produces greater acoustic power in relation to the electrical power supplied. An improved slew rate square waveform drive would also improve the node definition quality of the FSW, and an improved FSW further increases aerosol production.

In preferred embodiments, the acoustic energy sensor 44 can indicate a true representation of vibrational frequency and amplitude can be attached to the bottom of the main (i.e.: bottom) piezoelectric transducer 40 or 42 as illustrated to verify and monitor the presence of acoustic activity.

Also in preferred embodiments, the electrical feedback sensing wire 47 arrangement can be soldered to the main sliver screened anode and cathode areas independent of the power leads 46. The purpose of feedback sensor 47 is to monitor transducer component electrical integrity and enhanced electrical power output monitoring. This optional preferred arrangement ensures the integrity of the main power lead 64 arrangements. The thermal sensor 45 may also optionally be attached to the bottom of the bottom transducer 40, 42. The purpose of thermal sensor 45 is to monitor the temperature of the piezoelectric assembly and to prevent catastrophic drive and transducer failures due to piezoelectric overheating. The main purpose for monitoring and measurement transducer features is for pre and post production circuit integrity assessment and real-time closed-loop electronic output operation for precision control of aerosol production process.

Figure 5:
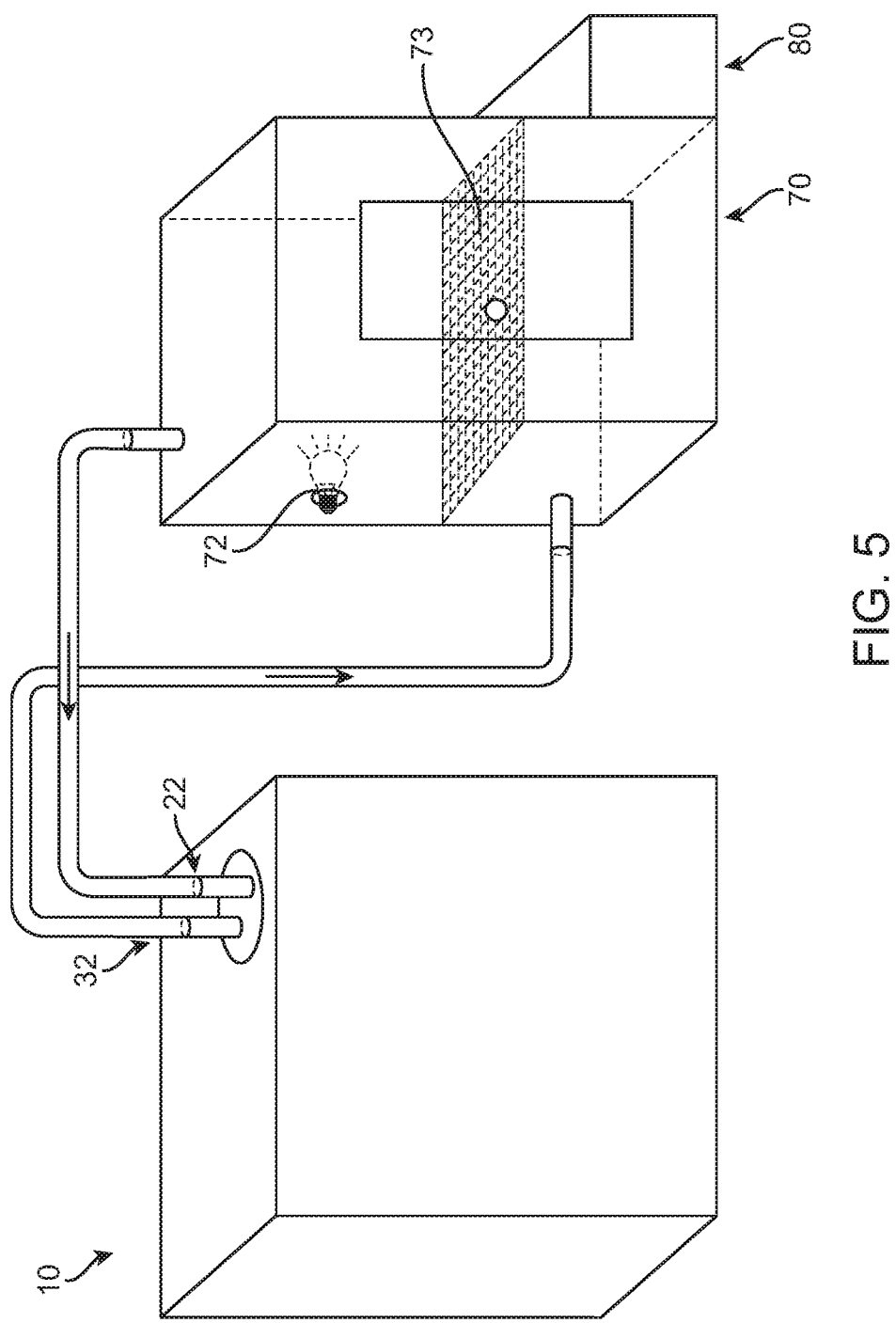
FIG. 5 is an illustration of the present aerosol production system used together with both an aerosol treatment chamber and an optional heating and dehumidification system.

FIG. 5 is an illustration of the present aerosol production system 10 used together with an aerosol treatment chamber 70 having an integrated optional heating and dehumidification system 80, as follows. Ultrasonic nebulization system 10 produces aerosol, as was described above. The aerosol from system 10 is then sent into aerosol treatment chamber 70. Specifically, the air preferably is recirculated through system 10 and treatment chamber 70. As more and more aerosol is produced by system 10, the concentration of aerosol in treatment chamber 70 will continue to increase. Visually, this will be seen as a "fog" in treatment chamber 70, with the density of the fog increasing over time. Objects to be sterilized, sanitized or disinfected with the aerosol can be placed inside aerosol treatment chamber 70.

Specifically, as illustrated in FIG. 5, aerosol treatment chamber 70 may comprise a large or small chamber optionally having a door 71 through which objects to be sterilized are placed in the chamber. Preferably, aerosol treatment chamber 70 may also include an internal shelf 73 onto which the objects to be sterilized or disinfected are placed. Internal shelf 73 may preferably comprise a wire shelf that permits the aerosol to freely circulate around the objects in the chamber.

It is to be understood that the same effect can be generated in an alternate set-up in which aerosol production system 10 is instead simple placed within treatment chamber 70, and simply turned on. In this alternate embodiment in which air continually recirculates though aerosol production system 10, treatment chamber can be a large enclosed structure, or even a sealed building room, all keeping within the scope of the present invention. It is therefore to be understood that the present invention is not limited to any particular type or dimension of treatment chamber 70.

In further optional embodiments, a heat source 72 may be disposed within aerosol treatment chamber 70 to cause the liquid droplet particles to vaporize into gaseous vapor. This heating approach has the advantage of decreasing sterilization times. For example, such heating can advantageously cause the particle size to be reduced from about 3 um by a factor of −10 to about 0.3-0.5 during this transition. As such, the sterilization time can preferably be shortened by about 50%. In addition to shortening the sterilization time, this optional heating of the aerosol production chamber 30 also reduces the amount of condensation on the surfaces within the aerosol production chamber. This results in a shorter "recovery" period between uses of the system. In various aspects, optional heating source 72 may be a radiant energy source including RF, IR or visible light range heating devices, or which IR heating is the most preferred to assist in quickly drying out aerosol treatment chamber 70 between uses.

Figure 6:
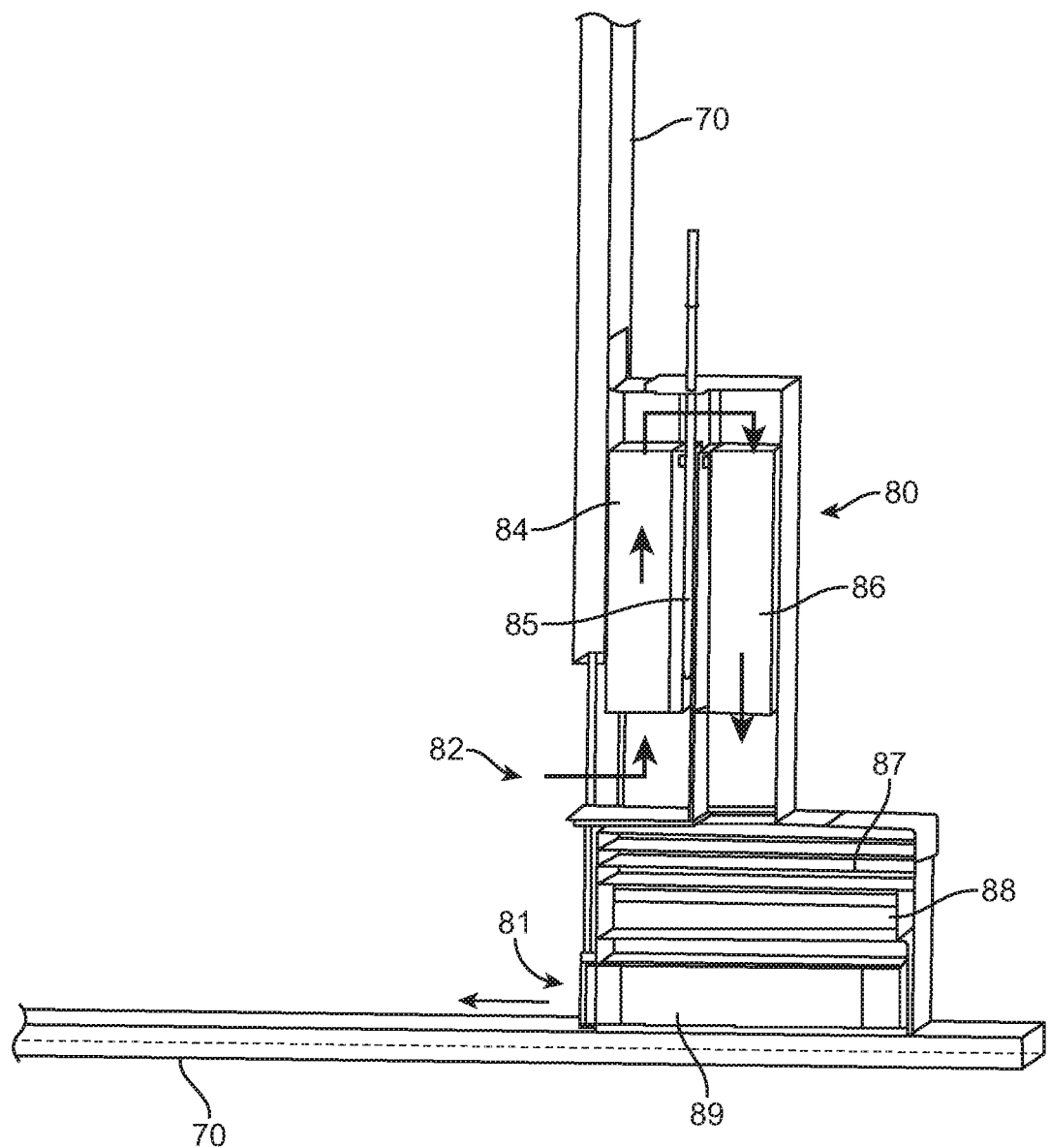
FIG. 6 is a close up sectional side elevation view of the optional Peltier heating and dehumidification system of FIG. 6.

In optional preferred embodiments as seen in FIGS. 5 and 6, an optional dehumidification and filtration system 80 can be attached to aerosol treatment chamber 70. For example, a Peltier-type dehumidification and filtration system 80 may be used. Specifically, such a dehumidification and filtration system 80 may be used for normalizing aerosol treatment chamber 70 air quality conditions after a disinfection cycle has been conducted. Treatment chamber 70's humidity and chemical particles can easily be removed by system 80, thereby quickly drying the aerosol treatment chamber prior to its reuse. Air passes from dehumidification and filtration system 80 into aerosol treatment chamber 70 at outlet 81, circulates through aerosol treatment chamber 70, and returns to dehumidification and filtration system 80 at inlet 82.

As best seen in FIG. 6, Peltier dehumidifier 80 includes appropriately sized heatsinks 84 and 86 connected to opposite sides of ceramic plate 85. As one side of dehumidifier 80 gets hot (e.g.: heatsink 86), an opposite side gets cold (e.g.: heatsink 84). When used with the present treatment chamber 70, air is dehumidified by the heatsinked Peltier cooler heatsink 84 (which condenses moisture drying the air). Next, the air passes over the Peltier warm side heatsink 86 (thereby heating and drying it). This warm dry air is then recirculated back into aerosol treatment chamber 70, thereby returning treatment chamber 70 back to ambient pre-treatment conditions. Optionally, the recirculating air may also be passed through a carbon filter 87 for chemical neutralization and a HEPA filter 88. A forced air recirculation fan 89 can be used to blow the hot dry air back into aerosol treatment chamber 70 at outlet 81. Alternatively, instead of fan 89, direct ventilation may be used.

What is claimed is:

1. An ultrasonic nebulization system, comprising:
   a master chamber;
   an aerosol production chamber received within the master chamber;

an air inlet into the master chamber;
an aerosol outlet out of the aerosol production chamber;
a liquid chamber at the bottom of the master chamber;
a baffle assembly positioned at the bottom of the aerosol production chamber;
a bottom ultrasonic transducer positioned below the liquid chamber; and
a top ultrasound transducer positioned above the liquid chamber in the aerosol production chamber; and
wherein the top and bottom ultrasound transducers are configured to generate standing waves therebetween within the aerosol production chamber.

2. The system of claim 1, wherein the master chamber is cylindrical and the aerosol production chamber is cylindrical and the aerosol production chamber is centered within the master chamber.

3. The ultrasonic nebulization system of claim 1, wherein air enters the aerosol production chamber after first passing between concentric walls of the aerosol production chamber and the master chamber.

4. The ultrasonic nebulization system of claim 1, wherein air enters the aerosol production chamber after passing across the baffle assembly.

5. The system of claim 4, further comprising spacers between the baffle assembly and the aerosol production chamber to provide an air passage across the top of the liquid chamber for air coming up into the aerosol production chamber.

6. The system of claim 1, wherein the top ultrasound transducer is positioned in a monitor assembly suspended from the top of the aerosol production chamber.

7. The system of claim 6, wherein the monitor assembly comprises a top cover that is positioned over the top ends of both the aerosol production chamber and the master chamber.

8. The system of claim 1, further comprising:
a bottom temperature sensor adjacent to the liquid chamber for sensing the temperature of the liquid, and
a top temperature sensor positioned in a monitor assembly for sensing the temperature of the aerosol.

9. The system of claim 1, wherein air enters the air inlet and aerosol exits the aerosol outlet.

10. The system of claim 1, wherein the aerosol outlet is positioned above the top center of the aerosol production chamber.

11. The system of claim 1, further comprising:
a treatment chamber that fills with aerosol from the aerosol outlet and is cleared of aerosol after a treatment cycle has been completed.

12. The system of claim 11, further comprising:
a heat source for warming the aerosol treatment chamber.

13. The system of claim 11, further comprising:
a dehumidification and filtration system that clears the treatment chamber of aerosol after the treatment cycle has been completed.

14. A method of generating an aerosol, comprising:
placing a liquid into a liquid chamber in an ultrasonic nebulization system;
passing air up through an aerosol production chamber in the ultrasonic nebulization system; and
generating standing waves above the surface of the liquid by applying an ultrasonic field with upper and lower ultrasonic transducers in the ultrasonic nebulization system, thereby generating an aerosol of the liquid by action of the standing waves.

15. The method of claim 14, wherein the standing waves are generated in an aerosol production chamber within the ultrasonic nebulization system.

16. The method of claim 15, wherein the aerosol production chamber is received within a master chamber, and air passes downwardly between walls of the aerosol production chamber and master chamber, and then passes upwardly through the center of the aerosol production chamber.

17. The method of claim 15, where the upper and lower ultrasonic transducers are positioned at the top and bottom of the aerosol production chamber respectively.

18. The method of claim 14, further comprising:
adjusting the lower transducer drive oscillating frequency to generate the standing waves.

19. The method of claim 14, further comprising:
directing the aerosol generated by the ultrasonic nebulization system into a treatment chamber to disinfect or sterilize an object in the treatment chamber.

20. The method of claim 19, further comprising at least one of:
heating the air within the treatment chamber after completing a disinfection cycle, or
dehumidifying the air within the treatment chamber after completing a disinfection cycle.

* * * * *